US008318911B2

(12) United States Patent
Anastasi et al.

(10) Patent No.: US 8,318,911 B2
(45) Date of Patent: Nov. 27, 2012

(54) ANTI-EPCAM ANTIBODY AND USES THEREOF

(75) Inventors: Anna Maria Anastasi, Pomezia (IT); Fiorella Petronzelli, Pomezia (IT); Rita De Santis, Pomezia (IT); Saverio Alberti, Lanciano (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 12/594,559

(22) PCT Filed: Apr. 2, 2008

(86) PCT No.: PCT/EP2008/053913
§ 371 (c)(1),
(2), (4) Date: Dec. 17, 2009

(87) PCT Pub. No.: WO2008/122551
PCT Pub. Date: Oct. 16, 2008

(65) Prior Publication Data
US 2010/0092491 A1 Apr. 15, 2010

(30) Foreign Application Priority Data
Apr. 4, 2007 (EP) .................................. 07105628

(51) Int. Cl.
*C07K 16/00* (2006.01)
*C12P 21/08* (2006.01)
*A61K 39/395* (2006.01)
*A61K 39/00* (2006.01)
*C07H 21/04* (2006.01)
*G01N 33/53* (2006.01)
*C12N 5/07* (2010.01)
*C12N 5/16* (2006.01)

(52) U.S. Cl. ............... 530/388.1; 530/387.1; 530/387.3; 424/130.1; 424/133.1; 424/141.1; 536/23.53; 435/7.1; 435/326

(58) Field of Classification Search .......................... None
See application file for complete search history.

(56) References Cited

U.S. PATENT DOCUMENTS
4,675,187 A 6/1987 Konishi et al.
5,578,287 A 11/1996 Theodore et al.
5,968,405 A 10/1999 Yamasaki et al.
2006/0105389 A1 5/2006 Kordyum et al.

FOREIGN PATENT DOCUMENTS
EP 0496074 12/1991
WO 94/04702 3/1994
WO 02/066075 8/2002
WO 2005/080428 9/2005

OTHER PUBLICATIONS

Rudikoff, Giusti, Cook, and Scharff. Single amino acid substitution altering antigen binding. Proceedings of the National Academy of Sciences, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin binding and mitogenic activities of heparin binding (acidic fibroblast) growth factor 1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Alberti, S. et al., "DNA methylation prevents transfection of genes for specific surface antigens", Proc. Natl. Acad. Sci., vol. 85, pp. 8391-8394, Nov. 1988.
Burak Jr., W.E. et al., Radioimmunoguided breast surgery using radiolabeled antibody NR-LU-10-FAB: a plot study, Tumori, 87, pp. 143-146, 2001.
Cianfriglia, M. et al., "Methods for high frequency production of soluble antigen-specific hybridomas; specificities and affinities of the monoclonal antibodies obtained", Methods in Enzymology, vol. 121, pp. 193-210, 1986.
De Bono, J. et al., "ING-1, a Monoclonal Antibody Targeting Ep-CAM in Patients with Advanced Adenocarcinomas" Clinical Cancer Research, vol. 10, pp. 7555-7565, Nov. 15, 2004.
Di Massimo ,A. M. et al., "Immunoconjugates made of an anti-EGF receptor monoclonal antibody and type 1 ribosome-inactivating proteins from *Saponaria ocymoides* or *Vaccaria pyramidata*", British Journal of Cancer, 75, pp. 822-828, 1997.

(Continued)

*Primary Examiner* — Anne Gussow
(74) *Attorney, Agent, or Firm* — Steinfl & Bruno LLP

(57) ABSTRACT

An anti-EpCAM antibody, designated ST3232/10, of marine origin exhibits properties suitable for both therapeutic and diagnostic applications. It shows high affinity for the native antigen and good tumor selectivity.

30 Claims, 9 Drawing Sheets

OTHER PUBLICATIONS

Figure 1:
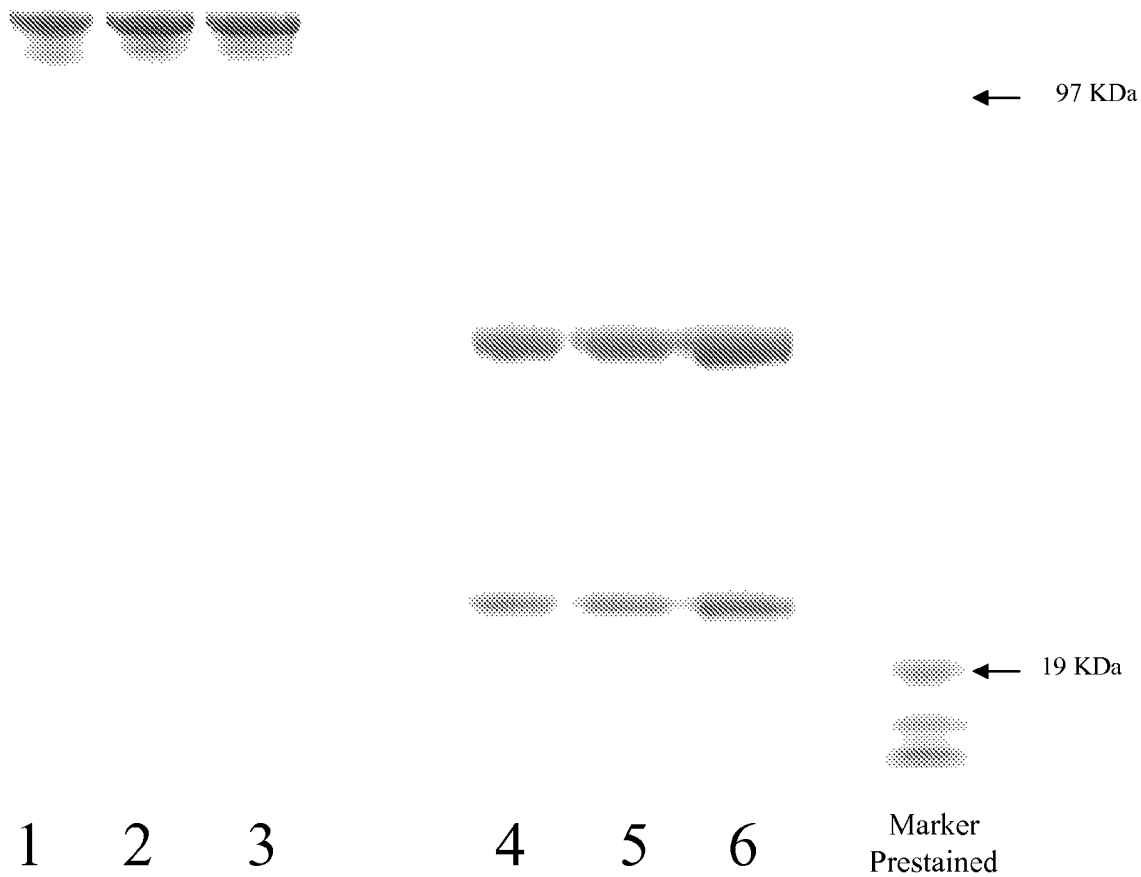

Ferrer, C. et al., "Expression and characterization of a mouse/human chimeric antibody specific for EGF receptor", Journal of Biotechnology, 52, pp. 51-60, 1996.

Frodin, J. E. et al., "MAb17 and Cytokines for the Treatment of Patients with Colorectal Carcinoma", Hybridoma and Hybridomics, vol. 21, No. 2, pp. 99-102, 2002.

Gearhart, P. J. et al., "Somatic Mutation and Affinity Maturation" Fundamental Immunology, Third Edition, pp. 865-885, 1993.

Goshorn, S. et al., "Preclinical Evaluation of a Human NR-LU-10 Antibody-Streptavidin Fusion Protein for Prertargeted Cancer Therapy", Cancer Biotherapy &Radiopharmaceuticals, vol. 16, No. 2, pp. 109-124, 2001.

Klein, C. E et al., " Expression of a 38-kD Cell-Surface Glycoprotein in Transformed Human Keratinocyte Cell Lines, Basal Cell Carcinomas, and Epithelial Germs", The Society for Investigative Dermatology, Inc, pp. 74-82, 1990.

Oberneder, R. et al., "A phase I study with adecatumumab, a human antibody directed against epithelial cell adhesion molecule, in hormone refractory prostate cancer patients", European Journal of Cancer, 42, pp. 2530-2538, 2006.

Old, L. J. et al., "Immunotherapy for Cancer", Scientific American, pp. 102-109,Sep. 1996.

Naundorf, S. et al., "In Vitro and in vivo activity of MT201, A fully human monoclonal antibody for pancarcinoma treatment", Int. J. Cancer, 100, pp. 101-110, 2002.

Paganelli, G. et al., "Antibody-guided three-step therapy for high grade glioma with yttrium-90 biotin" European Journal of Nuclear Medicine, vol. 26, No. 4, Apr. 1999.

Parente, D. et al., "Production and In Vitro characterization of a recombinani immunotoxin made of a single chain anti-egf receptor antibody and a type 1 ribosome-inactivation protein (RIP) from the filamentous fungus aspergillus clavatus", Abstract of the IIAR Conference on New Anticancer Agents, pp. 4073-1074, Oct. 12-15, 1997.

Penichet, M. L. et al., "An Antibody-Avidin Fusion Protein Specific for the Transferrin Receptor Serves as a Delivery Vehicle for Effective Brain targeting: Initial Applications in Anti-HIV Antisense Drug Delivery to the Brain", The Journal of Immunology, 4421-4426, 1999.

Prang, N. et al., " Cellular and complement-dependent cytotoxicity of Ep-CAM-specific monoclonal antibody MT 201 against breast cancer cell lines", British Journal of Cancer, 92, pp. 342-349, 2005.

Punt, C. J. A. et al., "Edrecolomab alone or in combination with fluorouracil and folinic acid in the adjuvant treatment of stage III colon, cancer: a randomized study" The Lancet, vol. 360, pp. 671-677, Aug. 31, 2002.

Riethmuller, G. et al., "Monoclonal antibody therapy for resected dukes' C Colorectal cancer: seven-year outcome of a multicenter randomized trial", Journal of Clinical Oncology, vol. 16, No. 5, pp. 1788-1794, May 1998.

Sassano, M. et al., "PCR amplification of antibody variable regions using primers tat annel to constant regions", Nucleic Acids Research, vol. 22, No. 9 , 1994.

Spizzo, G. et al., "High Ep-CAM expression is associated with poor prognosis in node-positive breask cancer", Breast Cancer Research and Treatment, 86, pp. 207-213, 2004.

Velders, M.P. et al., "The impact of antigen density and antibody affinity on antibody-dependent cellular cytotoxicity: relevance for immunotherapy of carcinomas" British Journal of Cancer, 78, (4), pp. 478-483, 1998.

Weiner, L. M. et al., "Phase II Multicenter Evaluation of Prolonged Murine Monoclonal Antibody 17-1A Therapy in Pancreatic Carcinoma", Journal of Immunotherapy, 13, pp. 110-116, 1993.

Went, P. et al., "Frequent high-level expression of the immunotherapeutics target Ep-CAM in colon, stomach, prostate and lung cancers", British Journal of Cancer, 94, pp. 128-135, 2006.

Winter,M. J. et al., "The Epithelial Cell Adhesion Molecule (Ep-CAM) as a Morphoregulatory Molecule Is a Tool in Surgical Pathology", American Journal of Pathology, vol. 163, No. 6, pp. 2139-2148, Dec. 2003.

International Preliminary Report on Patentability for PCT/EP2008/053913 filed on Apr. 2, 2008 in the name of SIGMA-TAU Industrie Farmaceutiche Riunite S.P.A.

International Search Report for PCT/EP2008/053913 filed on Apr. 2, 2008 in the name of SIGMA-TAU Industrie Farmaceutiche Riunite S.P.A.

EP Communication pursuant to Article 94(3) EPC for 08759374.5 filed on Apr. 2, 2008 in the name of SIGMA-TAU Industrie Farmaceutiche Riunite S.p.A.

Winkler et al., J Immunol 2000, 165:4505-4514.

EP Communication 71(3) issued for EP Application No. 08759374.5 filed on Apr. 2, 2008 in the name of SIGMA TAU mail date: Feb. 8, 2011.

EP Communication 97(1) issued for EP Application No. 08759374.5 filed on Apr. 2, 2008 in the name of SIGMA TAU mail date: May 19, 2011.

Paul, We, Somatic mutation and affinity maturation, Fundamental Immunology, Raven Press, NY, NY 1993, chapter 23.

De Santis et al., Low and High Tenascin-Expressing Tumors Are Efficiently Targeted by ST2146 Monoclonal Antibody, Clinical Cancer Research 2006, 12: 2191-2197.

Paganelli, et al., Pre-target locoregional radioimmunotherapy with $^{90}$Y-biotin in Glioma patients: Phase I study and preliminary therapeutic results, Cancer Biother. & Radiopharm. 2001, 16(3): 227-235.

Cremonesi, et al., Three-step radioimmunotherapy with yttrium-90 biotin: dosimetry and pharmacokinetics in cancer patients, Eur. J. Nucl. Med. 1999, 26(2): 110-120.

Derivative definition, retrieved on Dec. 16, 2011, from the Internet Archive Wayback Machine (Dec. 15, 2005); http://web.archive.org/web/20051215000000/http://en.wikipedia.org/wiki/Derivative_ (Ch . . . Dec. 16, 2011).

Derivative definition, retrieved on Dec. 16, 2011, from the Internet Archive Wayback Machine (Feb. 10, 2005); http://web.archive.org/web/20060210171407/http://www.biology-online.org/dictionary/d....

Derivative definition, Oxford Dictionary of Chemistry, 4$^{th}$ edition, 2000, p. 173.

* cited by examiner

A

B

ANTI-EPCAM ANTIBODY AND USES THEREOF

FIELD OF THE INVENTION

The present invention relates to anti-human EpCAM monoclonal antibodies and functional derivatives thereof, methods and materials for obtaining them, the use of said antibodies for the diagnosis and treatment of tumors expressing EpCAM and materials comprising said antibodies suitable for use in medical field.

BACKGROUND OF THE INVENTION

The targeting of tumor tissues by antibodies able to selectively recognize antigens overexpressed at the tumor site is the goal of all anti-tumor immunotherapies. Epithelial cell adhesion molecule (EpCAM, swiss prot no. P16422) also known as Tumor-associated calcium signal transducer 1, TROP-1, GA733-2, etc. is a type I trans-membrane glycoprotein expressed at the basolateral membrane on simple epithelia where it is involved in calcium-independent homophilic cell adhesion The extracellular domain consists of one epidermal growth factor like repeat, followed by a thyroglobulin repeat and a cystein poor region while the intracellular domain is 26 amino acids long and there are two binding sites for $\alpha$-actinin for linkage to the actin cytoskeleton (Winter M J et al. 2003). Cells from major human malignancies strongly overexpress EpCAM as recently confirmed by Went and coworkers (2006) that reported the immunohistochemistry results obtained on a large number of colon, gastric, prostate and lung tumor specimens. EpCAM overexpressing cells tend to segregate from normal cells, correlating with the development of a proliferative and malignant phenotype (Winter et al., 2003). Based on these data, the possibility to target EpCAM for immunotherapy was explored.

A murine IgG2a antibody, Edrecolomab, with some antibody dependent cellular cytotoxicity (ADCC) towards EpCAM positive cells, was approved in Germany for clinical use and employed for the treatment of patients with colorectal or pancreatic carcinoma who had undergone curative surgery. A seven-year follow up outcome of minimal residual disease after edrecolomab treatment in Dukes'C colorectal cancer patients showed a reduced mortality of 32% and a decrease in recurrence rate by 23% (Riethmuller G et al., 1998; Weiner L M et al., 1993). However, the overall results of the clinical study lead to the withdrawn of this drug as monotherapy, due to its limited antitumor efficacy (Punt C J, et al., 2002) and to the promotion of new clinical trials where the antibody is intended in adjuvant settings with other active chemotherapeutic compounds (Frodin J E et al., 2002).

Other antibodies against this target have been used in preclinical or clinical settings. MT-201 (Adecatumumab) is a fully human monoclonal IgG1 antibody with moderate affinity for EpCAM (Naundorf S et al., 2002). Its efficacy was demonstrated in nude mouse xenograft model using the colon cancer cell line HT-29 (Naundorf S et al., 2002). In vitro studies on various tumor cell lines have shown that MT201 mediates target cell lysis by ADCC and complement dependent cytotoxicity (CDC) (Prang N et al., 2005). This antibody is currently under clinical development for the treatment of hormone refractory prostate cancer (Oberneder R et al., 2006).

ING-1 is a high affinity human engineered monoclonal antibody that targets EpCAM positive cells. It has been used in a phase I clinical trial in patients with advanced adenocarcinomas, refractory to standard therapy and the data from this study suggested that antibodies with high affinity to EpCAM, while being more cytotoxic to tumor cells, can also induce rapid pancreatic toxic injury thus, limiting their therapeutic window for systemic administration (De Bono J S et al., 2004). There are diverging opinions on the relevance of antibody affinity for the efficacy of immunotherapy. Velders et al. (1998) presented in vitro data on the impact of antibody affinity and antigen density on ADCC as obtained by comparison of two antibodies having different affinity for EpCAM. Data obtained from this study revealed that the high affinity antibody could mediate cell killing with low antigen expression levels or, at comparable binding levels, with higher efficacy. As heterogeneity of a target antigen expression is a common feature of all tumors, the use of high affinity antibodies could improve clinical results. The possible systemic toxic effects, associated with the therapeutic use of high affinity anti-EpCAM antibodies, might be reduced by pre-targeting strategies which include a chasing step to eliminate, at a given time, the circulating antibody. Alternatively, the use of high affinity anti-EpCAM antibodies might be restricted to loco-regional treatments.

A humanized single chain Fv antibody fragment, NR-LU-10, specific to the EpCAM antigen, genetically engineered as a streptavidin fusion protein has been developed for pretargeted radioimmunotherapy or radioimmunoguided breast surgery. Preclinical data showed that a single dose of 800 μCi of 90Y-DOTA-biotin administered after NR-LU-10, cured mice with established subcutaneous human small cell lung or colon cancer xenograft (Goshorn S et al., 2001). In a second report by Burak W E Jr et al. (2001) the use of labeled NR-LU-10 Fab was useful in intra-operative probing for revealing tumor localization in 7 out of 10 patients, thus confirming its ability as a targeting agent.

Despite the clinical success of monoclonal antibodies in several pathologies, the immunotherapy of solid tumors still remains unsatisfactory. Pretargeted Antibody Guided Radio-ImmunoTherapy (PAGRIT™) is a multi-treatment approach allowing restricted and amplified accumulation of the radio-isotope in the tumor. The specificity and affinity of the anti-tumor monoclonal antibody, used as a first step, is fundamental for treatment efficacy.

The Applicant reported exceptionally high and specific accumulation of the ST2146 anti-tenascin monoclonal antibody in both low and high antigen-expressing human xenotransplanted tumors (De Santis et al., Clinical Cancer Research, p. 2191, 1 Apr. 2006).

Based on the teaching of EP 0 496 074, G. Paganelli et al developed this three-step pre-targeting approach for the systemic and loco-regional treatment of tumors (Cremonesi M. et al., Eur. J. Nucl. Med. 26 (2).-110-120, 1999; Paganelli G. et al., Eur. J. Nucl. Med. 26 (4): 348-357, 1999; Paganelli G., et al. Cancer Biother. & Radiopharm. 16 (3): 227-235, 2001).

Other references on the three-step pre-targeting method are WO 94/04702 and U.S. Pat. No. 5,578,287.

The three step pre-targeting treatment is based on intravenous, sequential administration of a biotinylated anti-tenascin monoclonal antibody, streptavidin, and $^{90}$Y-labelled biotin with two chasing administrations of avidin and biotinylated albumin before streptavidin and $^{90}$Y-labelled biotin, respectively, to reduce non specific background.

In the medical field, there is a need for further and improved anti-EpCAM antibodies useful in cancer diagnosis and therapy, such as for example in the PAGRIT approach.

SUMMARY OF INVENTION

The present invention relates to an antibody and antibody fragments which may also contain additional moieties and diagnostic agents, compositions containing these antibodies and antibody fragments, and diagnostic and therapeutic compositions containing them, their use in therapy and diagnostics and methods of making these antibody and antibody fragments.

It is an object of the present invention an anti-EpCAM antibody or a functional derivative thereof wherein the variable region of the antibody heavy chain comprises at least one of the complementarity determining regions (CDRs) having the sequence selected from SEQ ID No.2; SEQ ID No. 4 or SEQ ID No. 6.

Preferably, the variable region of the antibody heavy chain comprises at least two of the complementarity determining regions (CDRs) having the sequence of SEQ ID No.2; SEQ ID No. 4 or SEQ ID No. 6.

Still preferably, the variable region of the antibody heavy chain comprises all three complementarity determining regions (CDRs) having the sequence of SEQ ID No.2; SEQ ID No. 4 and SEQ ID No. 6.

It is a further object of the invention an anti-EpCAM antibody or functional derivative thereof wherein the variable region of the antibody light chain comprises at least one of the complementarity determining regions (CDRs) having the sequence of SEQ ID No.8; SEQ ID No. 10 or SEQ ID No. 12.

Preferably, the variable region of the antibody light chain comprises at least two of the complementarity determining regions (CDRs) having the sequence of SEQ ID No.8; SEQ ID No. 10 or SEQ ID No. 12.

More preferably, the variable region of the antibody light chain comprises all three complementarity determining regions (CDRs) having the sequence of SEQ ID No.8; SEQ ID No. 10 and SEQ ID No. 12.

It is a further object of the invention an anti-EpCAM antibody or functional derivative thereof having the variable region of heavy chain comprising at least one, two or all of the sequences of SEQ ID No.2; SEQ ID No. 4 or SEQ ID No. 6 and the variable region of the light chain comprising at least one, two or all of the sequences of SEQ ID No.8; SEQ ID No. 10 or SEQ ID No. 12.

Preferably, the anti-EpCAM antibody or functional derivative thereof according to the invention is able to completely and permanently inhibit growth of EpCam expressing tumors.

The invention also contemplated the generation of mutants of the disclosed CDRs by mutating one or more amino acids in the sequence of the CDRs. It is known that a single amino acid substitution appropriately positioned in a CDR can be sufficient to improve the affinity. Researcher have used site directed mutagenesis to increase affinity of some immunoglobulin products by about 10 fold. This method of increasing or decreasing (i.e modulating) affinity of antibodies by mutating CDRs is common knowledge (see, e.g., Paul, W. E., 1993). Thus, the substitution, deletion, or addition of amino acids to the CDRs of the invention to increase or decrease (i.e, modulate) binding affinity or specificity is also within the contemplation of this invention.

For sake of brevity, the preferred antibody according to the present invention shall be identified with the name ST3232/10. While the present invention focuses on ST3232/10, as an exemplification of the present invention, one of ordinary skill in the art will appreciate that, once given the present disclosure, other similar antibodies, and antibody fragments of ST3232/10, as well as antibody fragments of these similar antibodies may be produced and used within the scope of the present invention. Such similar antibodies may be produced by a reasonable amount of experimentation by those skilled in the art.

Preferably the anti-EpCAM antibody is a monoclonal antibody. More preferably it is produced by the hybridoma cell line deposited according to the Budapest Treaty at the Advanced Biotechnology Center, Genoa, Italy, under No. PD06004.

Still preferably, the antibody is a scFv, Fv fragment, a Fab fragment, a F(ab)2 fragment, a multimeric antibody, a peptide or a proteolytic fragment containing the epitope binding region.

Yet preferably, the antibody is chimeric, fused to another protein or linked to an agent or a marker. More preferably, the chimeric protein is a mouse-human chimera.

Preferably, the fusion protein comprises a cytokine, a protein of the avidin family, biotin, labelled biotin or other effector proteins.

The antibody, antibody fragment, antibody chimera or immunoglobulin products of the invention may be linked to an agent. Linkage may be by covalent bonds or by antibody-epitope bond. For example, an antibody, antibody fragment, antibody chimera or immunoglobulin products may be crosslinked to a second antibody wherein the second antibody may have an affinity for the agent. The agent may be a cytotoxic agent. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof. The agent may be a chemotherapeutic agent. A chemotherapeutic agent is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards. The agent may be a cytokine. The term cytokine is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon-.alpha., -.beta., and -.gamma., colony stimulating factors (CSFs); granulocyte-macrophage-C-SF (GM-CSF); and granulocyte-CSF (G-CSF); interleukins (ILs) such as IL-1, IL-1.alpha., IL-2, IL-3, IL-4, IL-5, IL-6, IL-7, IL-8, IL9, IL-11, IL-12; a tumor necrosis factor; and other polypeptide factors including LIF and kit ligand (KL). As used herein, the term cytokine includes proteins from natural sources or from recombinant cell culture and biologically active equivalents of the native sequence cytokines.

For diagnosis, the antibody, antibody fragment, antibody chimera or immunoglobulin products of the invention may be attached to a label, such as to a detectable compound or composition which is conjugated directly or indirectly to the antibody. The label may be detectable by itself (e.g. radioisotope labels or fluorescent labels) or, in the case of an enzymatic label, may catalyze chemical alteration of a substrate compound or composition which is detectable.

More preferably, the antibody is a human or humanised antibody.

The present invention therefore provides an antibody or antibody fragment or antibody chimera (such as, for example, a mouse-human chimera or a fusion protein with molecules like cytokines, protein of the avidin family or other effector proteins) or immunoglobulin molecule which specifically binds EpCAM. The present invention provides an antibody or antibody fragment or antibody chimera or immunoglobulin molecules comprising at least one of the CDR of the variable light chain of ST3232/10 and/or a CDR of the variable heavy chain of ST3232/10. The antibody or antibody fragment or antibody chimera or immunoglobulin molecules of the present invention may be an antibody, an Fv fragment, an Fab fragment, a $F(ab)_2$ fragment, a single chain antibody, or a multimeric antibody. The antibody or antibody fragment or antibody chimera or immunoglobulin molecules of the present invention may be or be derived from IgM, IgD, IgG, IgA, or IgE isotypes.

Another object of the present invention are the recombinant derivatives of said antibody. In particular, preferred recombinant derivatives are those where the murine constant region is replaced by the human counterpart (Ferrer C. et al., 1996) or those where the murine constant region is replaced by a biologically active moiety, such as, for example, a member of the avidin family (Penichet M L et al., 1999), a growth factor useful for stimulating tumor-directed immunological effectors (such as for example G-CSF, GM-CSF), or those wherein the murine constant region is replaced by a pharmacologically active moiety, such as for example a toxin, a superantigen, a cytokine or any other protein useful in enhancing the antitumor therapeutical efficacy (Di Massimo A. M. et al., 1997; Parente D. et al., 1997).
The methods for obtaining said recombinant derivatives are well-known in the art.

Another object of the present invention are the conjugate derivatives of said antibody.

In particular, preferred conjugate derivatives are those where biologically active moiety are linked to the antibody by way of conventional methods. Examples of biologically active moieties are member of the avidin family, a growth factor useful for stimulating tumor-directed immunological effectors (such as for example G-CSF, GM-CSF), a pharmacologically active moiety, such as for example a toxin, a superantigen, a cytokine or any other protein useful in enhancing the antitumor therapeutical efficacy, antitumor drugs, radioisotopes.

According to the present invention, recombinant derivatives or conjugates of the monoclonal anti-human EpCAM or fragments thereof are also indicated as "derivatives". In a most particularly preferred embodiment of the invention, other than the antibody and the fragments, also the derivatives thereof are biotinylated.

It is a further object of the present invention a nucleic acid encoding the antibody or functional derivatives thereof of the invention, or hydridizing with the above nucleic acid, or consisting of a degenerated sequence thereof.

Preferably, the nucleic acid comprises at least one of the following sequences: SEQ ID No. 1, SEQ ID No. 3, SEQ ID No. 5, SEQ ID No.7, SEQ ID No. 9 and SEQ ID No. 11.

Another embodiment is directed to a purified nucleic acid molecule encoding the antibody or antibody fragment or antibody chimera or immunoglobulin molecule products of the invention. A nucleic acid molecule encoding an immunoglobulin product of the invention may be made using conventional techniques. For example, oligonucleotides may be synthesized using oligonucleotide synthesizers and ligated together to form a functional open reading frame that encodes an immunoglobulin product of the invention. The nucleic acid molecule, once synthesized, may be cloned into a nucleic acid vector. A nucleic acid vector such as a plasmid, cosmid, phagemid, yeast plasmid, phage vectors, TI plasmid and the like are known in the art. The vector may be an expression vector. Expression vectors and expression systems are available commercially from suppliers such as Stratagene (La Jolla, Calif.).

It is another object of the invention an expression vector comprising the nucleic acid of the invention.

It is a further object of the invention a host cell transformed with the expression vector of the invention.

The cell may be made by transfection. Methods of transfection are known and kits for transfection of prokaryotic and eukaryotic cells may be purchased from commercial sources (e.g., Stratagene, La Jolla, Calif.).

It is another object of the invention an hybridoma cell line producing the anti-EpCAM antibody of the invention. Preferably, the hybridoma cell line is the hybridoma cST3232/10 deposited according to the Budapest Treaty at the Advanced Biotechnology Center, Genoa, Italy, under No. PD06004.

The process for the preparation of the monoclonal antibody is within the skills of the man skilled in the art and comprises cultivating the above hybridoma cell line and isolating the antibody according to standard procedures.

It is an ulterior object of the invention the anti-EpCAM antibody of the invention for use as a medicament. Preferably, for use as an anti-tumour medicament. More preferably, the tumour is selected from the group of: colon carcinoma, breast carcinoma, gastric carcinoma, ovary carcinoma, urinary bladder carcinoma or lung carcinoma. Another embodiment of the invention is directed to a method of treating a patient with a neoplastic disorder comprising administering an antibody, antibody fragment, antibody chimera or immunoglobulin product of the invention or a nucleic acid of the invention to said patient. Methods for immunotherapy for cancer are known. See for example in Old, L. J. Immunotherapy for Cancer, Scientific American, September 1996 The antibody could be conjugated to biotin and removed from the circulation by using a chasing agent such as avidin in order to prevent possible toxic effect of the systemic administration.

Also disclosed herein is a method of treating a solid tumor which comprises, first, removing a solid tumor (e.g., one which expresses EpCAM) from a solid tissue organ (e.g., the colon) of an afflicted human subject and then administering to the subject an anti-neoplastic agent such as an antibody, antibody fragment, antibody chimera or immunoglobulin product of the present invention (e.g., an antibody that binds to EpCAM) which is selectively toxic to the cells of the solid tumor in a therapeutically effective amount. In an embodiment of the invention, the administering step is carried out by depositing the antineoplastic agent in the resection cavity.

It is a further object of the invention a pharmaceutical composition comprising an effective amount of the antibody or derivatives thereof according to the invention and a pharmaceutically acceptable carrier or diluent. Preferably, the pharmaceutical composition of the invention is for radioimmunotherapy. Pharmaceutical compositions are conventional in this field and can be made by the person skilled in the art just based on the common general knowledge. Examples of pharmaceutical compositions are given in the references mentioned in the present invention. The same applies to diagnostic kits. Particularly preferred in the kit for radioimmunotherapy of tumors as disclosed in the above mentioned papers by Paganelli et al. and EP 0 496 074.

Pharmaceutical compositions comprising the antibody and/or a fragment and/or a recombinant derivative and/or a conjugate thereof in admixture with at least one pharmaceutically acceptable excipient and/or vehicle are included in the scope of the present invention.

Still another aspect of the present invention is a medicament for the radioimmunotherapy of tumors, which is administered to a subject suffering from a tumor expressing EpCAM, and comprises said monoclonal antibody or proteolytic fragments, or derivatives thereof. In a preferred embodiment, said monoclonal antibody or proteolytic fragments or derivatives thereof are biotinylated, in a more particularly preferred embodiment, the medicament is suitable for radioimmunotherapy, in particular for carrying out the three-step pre-targeting method, as described in the art, for example in EP 0 496 074, Paganelli et al., 1999 and U.S. Pat. No. 5,968,405. In this latter aspect, the medicament according to the present invention shall be in the form of a kit, said kit being composed of 4 vials, whose first vial contains the biotinylated antibody or fragment or derivative thereof, the second vial contains an avidin, the third vial contains biotinylated albumin, the fourth vial contains radiolabelled biotin or biotin derivative. Such a kind of kit is provided in Paganelli et al., 1999. An avidin comprises avidin, streptavidin, PEG-avidin or PEG-streptavidin, di- or polyavidin or di- or polystreptavidin wild type or deglycosylated. A radio labelled biotin contains a radionuclide, such as disclosed in EP 0 496 074, preferably $^{90}$Y Biotin derivatives are disclosed, for example in WO 02/066075. A kit of this kind is disclosed in Paganelli et al., 1999. Preferably, the vials are suitable for human injection.

Preferably the composition comprises, in the same unit dose or separately, at least another tumour specific antibody. Preferably the tumour specific antibody is an EpCAM antibody different from the antibody of the invention. Another embodiment is directed to a therapeutic composition comprising an antibody, antibody fragment, antibody chimera or immunoglobulin product of the invention. The immunoglobulin products of the invention may be provided in the form of a composition comprising the antibody, antibody fragment, antibody chimera or immunoglobulin product and a pharmaceutically acceptable carrier or diluent. The therapeutic composition may be used for the treatment of disorders in a mammals such as a human. The invention also provides a method for treating a mammal comprising administering a therapeutically effective amount of the antibody, antibody fragment, antibody chimera or immunoglobulin product of the invention to the mammal, wherein the mammal has a disorder, such as cancer, requiring treatment with the antibody, antibody fragment, antibody chimera or immunoglobulin product.

It is another object of the invention the anti-EpCAM antibody of the invention for use in diagnostics. Preferably, as an anti-tumour diagnostic. More preferably, as an anti-tumour diagnostic in vivo. The detection or diagnosis of a disorder may comprise the steps of targeting a tissue sample from a subject with the antibody, antibody fragment, antibody chimera or immunoglobulin product of the invention under condition that permits the formation of a complex between said antibody, antibody fragment, antibody chimera or immunoglobulin product and the EpCAM antigen, and determining the formation of said complex. The antibody according to the invention may be applied to various types of immunological or biochemical diagnosis techniques. For example, the diagnosis techniques include (1) use of a fluorescent antibody or a chemical staining method in which the monoclonal antibody is labelled with dye, such as a fluorescent dye, to allow the presence of the linkage between the monoclonal antibody and the antigen to be visibly observed, (2) an enzyme-antibody method using an enzyme instead of the fluorescent dye to label the monoclonal antibody, (3) an ELISA method using a protein-labelled secondary antibody to measure an amount of antigen or the like, (4) a radioimmunoassay method in which the monoclonal antibody is labelled with isotope, and (5) an immunoprecipitation method utilizing an agglutination reaction caused by the antigen-antibody reaction.

The diagnosis techniques further include a Western blotting method in which proteins are fractionated through electrophoresis, and detected by the monoclonal antibody. The Western blotting method is advantageous in the direct cloning of a polynucleotide encoding the antigen protein with respect to the monoclonal antibody. The Western blotting method includes various modifications, such as a Western method, a South Western method, a North Western method, and a West Western method.

In another embodiment of the present invention, the antibody and the fragments thereof can further contain additional markers and/or diagnostic agents. Said markers and/or diagnostic agents are well-known to the person skilled in the art which the present invention is directed to. According to a preferred embodiment of the present invention, said antibody or proteolytic fragments thereof are biotinylated.

It is a further object of the invention an injectable soluble composition for in vivo tumour diagnostics comprising the anti-EpCAM antibody of the invention.

It is a further object of the invention a method for immunodetecting in a sample an antigen able to bind to the antibody or derivative thereof according to the invention comprising the step of incubating in proper condition the sample with the antibody or derivative thereof according to claims 1 to 14 to have an antigen-antibody complex, and detecting the antigen-antibody complex.

It is a further object of the invention a diagnostic kit for the method according to claim 30 comprising an antibody or derivative thereof according to claims 1 to 14 and antigen-antibody complex detecting means.

In another embodiment of the present invention, in the therapeutic kit, the biotinylated antibody is combined with other EpCAM-specific antibodies. Alternatively, the biotinylated antibody is combined with other tumor specific antibodies. A general teaching of said kind of kit is provided in EP 0 496 074, Paganelli et al., 1999 and U.S. Pat. No. 5,968,405.

In particular, the present invention also encompasses a container, optionally containing multiple compartments, comprising the biotinylated antibody or fragments or derivatives thereof, buffers and reagents suitable for use in a therapeutic kit for a three-step pre-targeting method.

Another object of the present invention is the use of said monoclonal antibody or fragments, or recombinant derivatives or conjugates thereof or the biotinylated derivative thereof, for the preparation of diagnostic means, for the detection of diseases expressing EpCAM, in particular for in vivo imaging of tumor.

ST3232/10 is obtained from the corresponding hybridoma cell clone cST3232/10 as given in detail in the following example.

As far as the industrial aspects of the present invention are concerned, the antibody herein disclosed shall be suitably formulated in pharmaceutical compositions or diagnostic kits as normally done in this technical field.

The present invention shall be disclosed in detail in the following description also by means of non limiting examples referring to the following figures.

FIG. 1: 4-12% BisTris SDS-PAGE (Precast, Invitrogen, USA) of cST3232/10 harvest purified on protein A column (MabSelect SuRe, GE Healthcare). Lanes 1-3: purified ST3232/10 Mab under not reducing conditions; lanes 4-6: purified ST3232/10 Mab under reducing conditions. Running buffer 1×MES. Gel staining by comassie (Simplie Blu, Invitrogen, USA)

Figure 2:
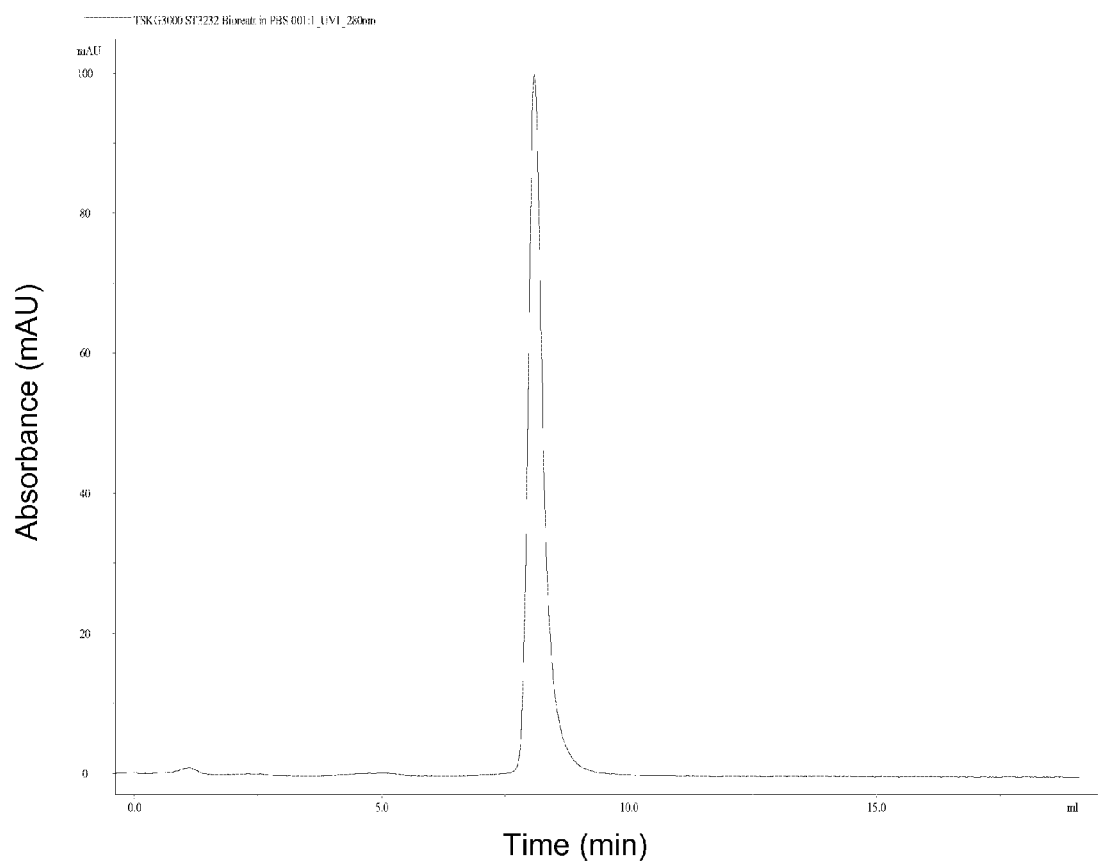

FIG. 2: Gel-Filtration on TSGK3000 column of purified ST3232/10, run in PBS pH 7. Time (min) is reported in abscise and milli absorbance units (mAU) in ordinate.

Figure 3:
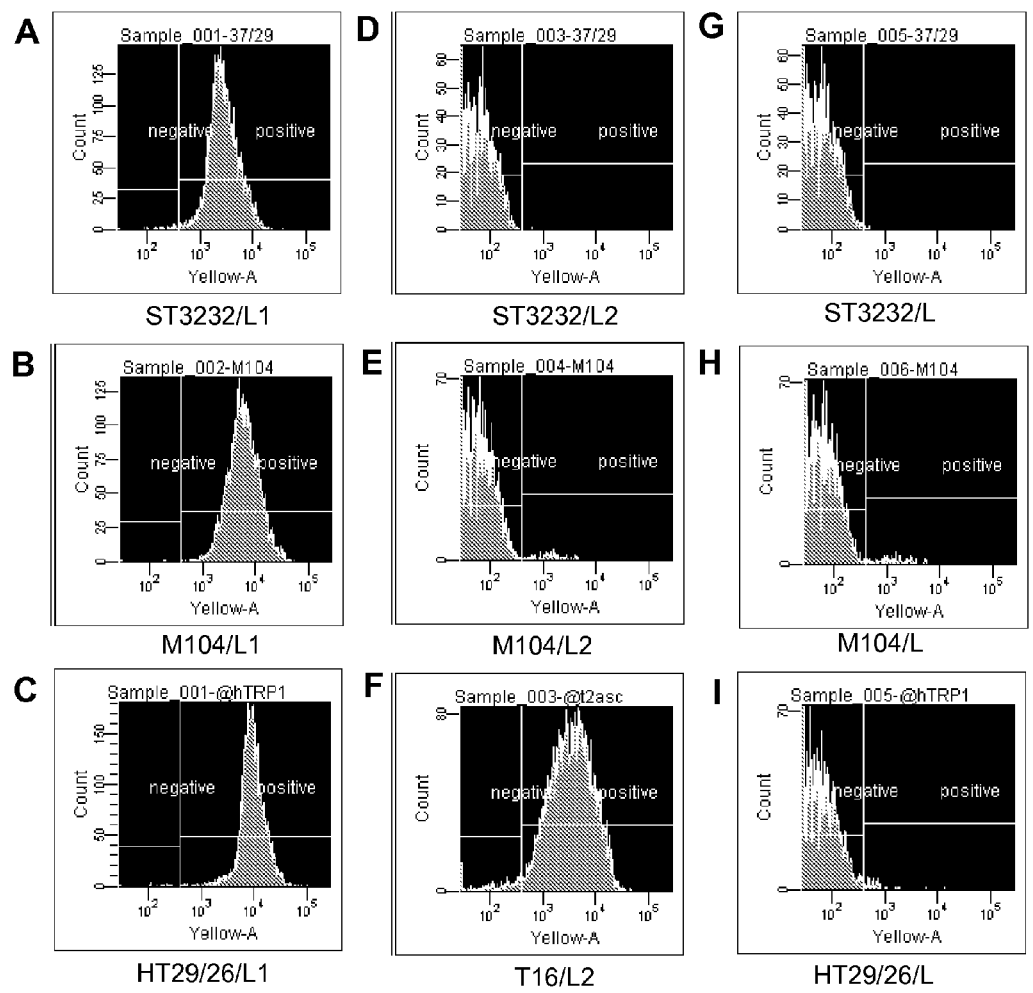

FIG. 3: FACS specificity test of anti EpCAM antibodies. ST3232/10 or other control antibodies (M104, HT29/26 and T16) were incubated (1 µg/$10^6$ cells, 1 h 4° C.) with murine fibrosarcoma L cells not naturally expressing EpCAM, transfected with human TROP-1 molecule (panels A-C), human TROP2 molecule (panels D-F) or with the empty vector where no exogenous proteins were introduced (panels G-I). A secondary PE-conjugated antibody (BD, USA) was used according to manufacturer instructions and cell mortality was evaluated by staining with 7-AAD (FACSCalibur, BD Biosciences, USA). ST3232/10 showed positive with the TROP-1 positive cells (panel A) and negative with the wild type L cells or with those transfected with the TROP2 molecule (panels G and D, respectively). A similar result was observed with other EpCAM specific antibodies (panels B, E, H: M104; C, I: HT29/26). T16 antibody was used as positive control in TROP2-L cells (panel F).

Figure 4:
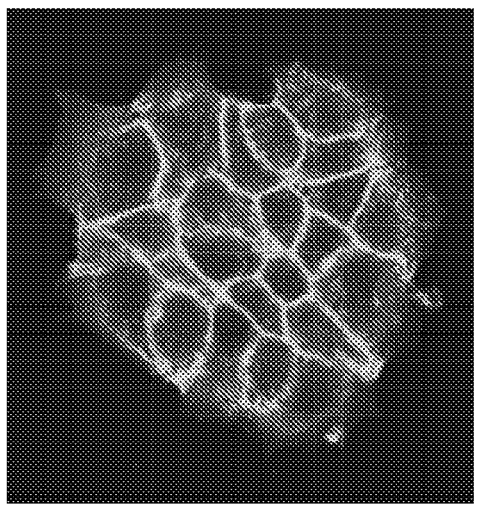
Figure 4:
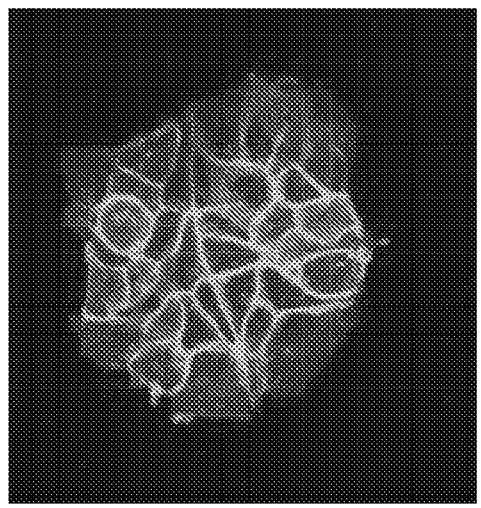

FIG. 4: Confocal microscopy of ST3232/10 conjugated with Alexa488 on MCF7 breast tumor cell line. MCF7 cells were plated on 15×15 mm coverslips, and fixed after 48 h by incubation in PBS/4% paraformaldehyde for 30 min at RT. The cells were then permeabilized and stained with the antibody, and several fields analyzed by confocal microscopy. The Alexa488-ST3232 conjugate demonstrates the expected pattern of staining, with highest intensity at cell-cell borders, and staining of isolated patches. Two examples of isolated patches are reported in panels A and B.

Figure 5:
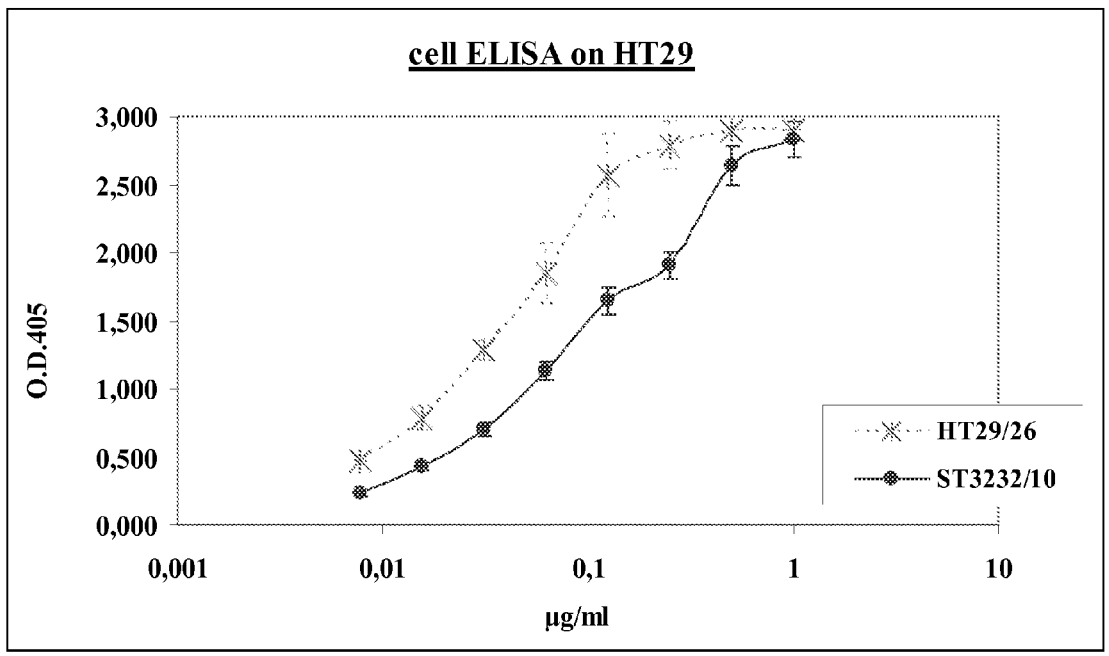

FIG. 5: Immunoreactivity of ST3232/10 and the monoclonal antibody HT29/26 anti EpCAM towards the antigen expressed on HT29 colon carcinoma cell line. Data are represented as the optical density (OD, measured at 405 nm) variation (linear scale, Y axis) at increasing concentrations of the two antibodies (µg/ml, logarithmic scale, X axis) incubated with HT29 colon carcinoma.

Figure 6:
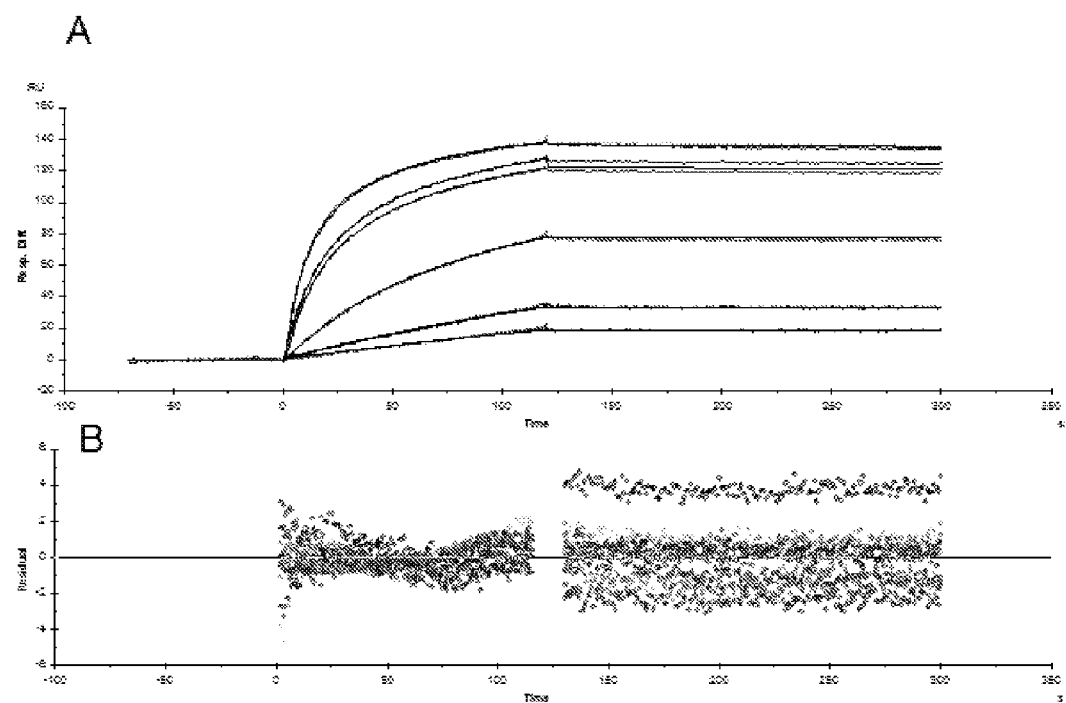

FIG. 6: Kinetic analysis and parameters of ST3232/10 binding to the extracellular domain of the EpCAM molecule immobilized on a CM5 sensor chip. Panel A: sensorgrams of the Mab injected concentrations (500, 250, 62.5, 15.6 and 7.8 nM) as function of time (min, X axis) and resonance units (RU, Y axis). Panel B: a bivalent model in the BiaEvaluation software was used for data fit; the residuals, representing the difference in RU between observed and expected curves, are reported in the graph (Y axis) for each time point (X axis). The kinetic constants are the following: $ka_1$=7.75E+04±297, $kd_1$=7.20E−05±8.48E−06, $K_D$=9.3E−10, $\chi^2$=1.97.

Figure 7:
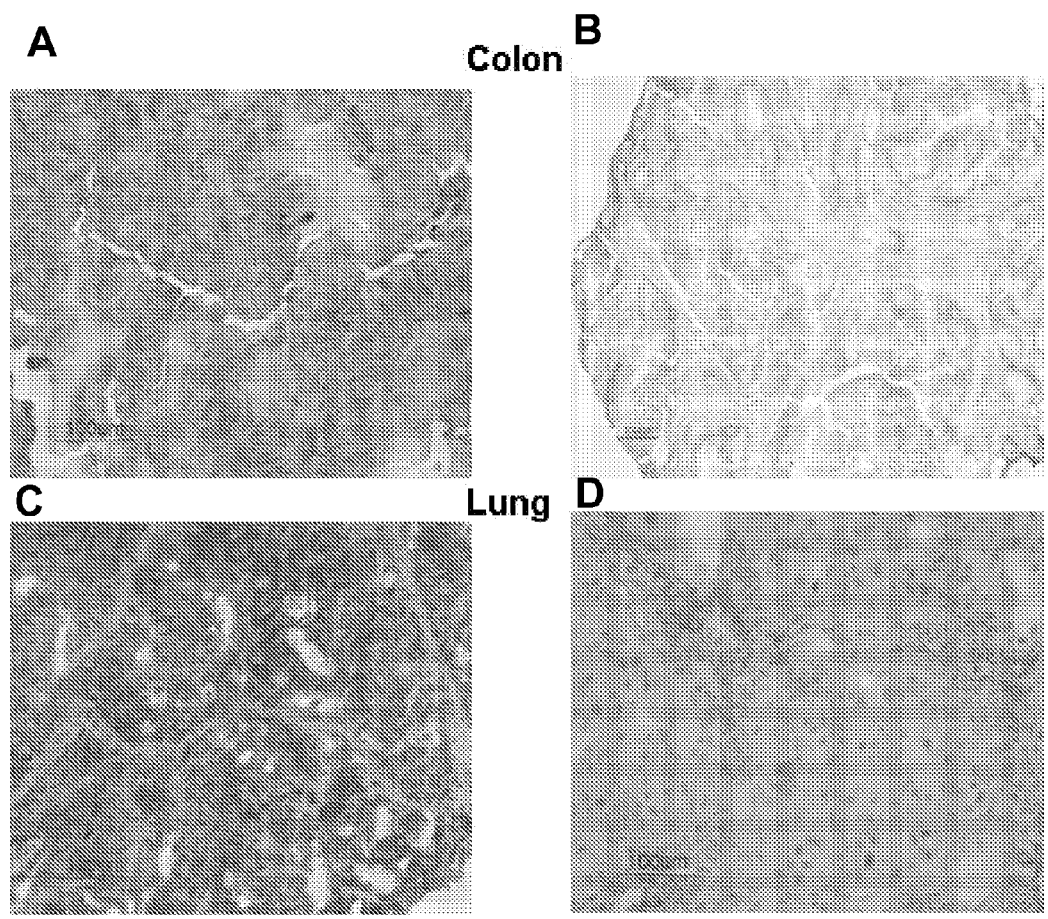

FIG. 7: ST3232/10 reactivity on human tumor and normal tissues. As an example, the immunohistochemistry results on colon and lung carcinoma (panels A and C, respectively) are shown in comparison to their normal counterparts (panels B and D, respectively). Human tumor tissues are strongly stained.

Figure 8:
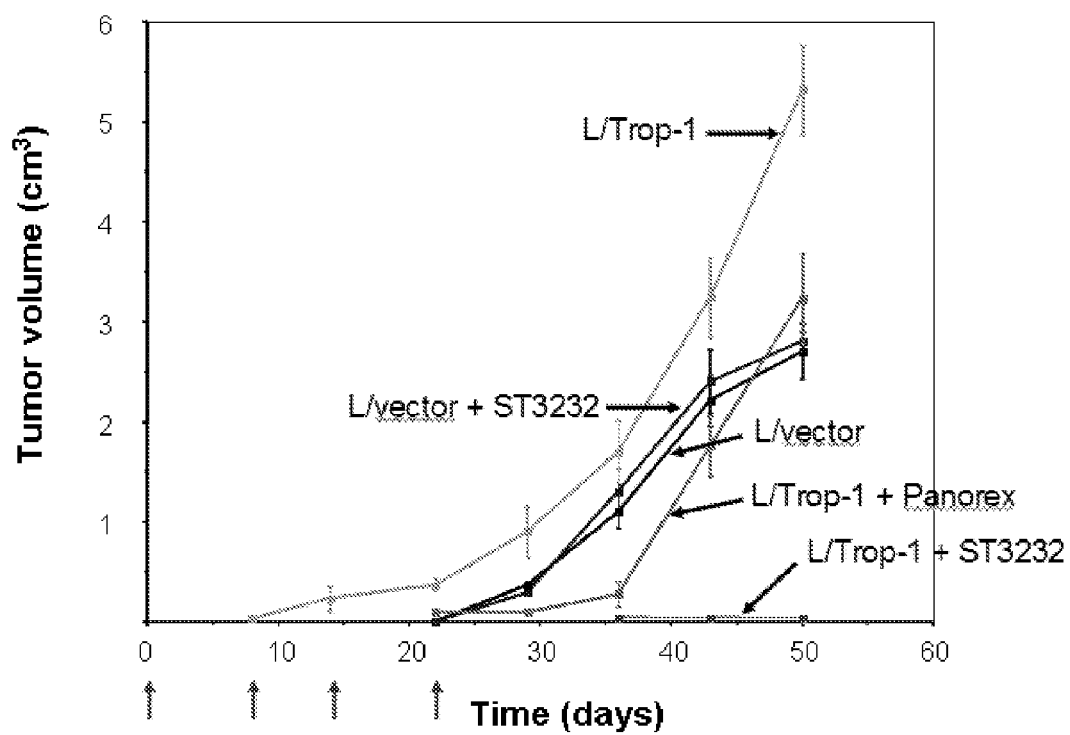

FIG. 8: Allogenic transplant in nude mice and treatment with ST3232/10 in comparison with Edrecolomab (Panorex®). The murine L fibrosarcoma cell line, transfected (L/Trop-1) or not transfected (L/vector) with human Trop-1, was subcutaneously injected in nude mice. The day of the inoculum the animals were treated with 200 µg of ST3232/10 (L/vector+ST3232 and L/Trop-1+ST3232), Edrecolomab (L/Trop-1+Panorex) or unrelated murine IgG (L/vector and L/Trop-1). Other three administrations were performed at day 7, and 22 as indicated by the arrows. Tumor progression was monitored until day 50.

Figure 9:
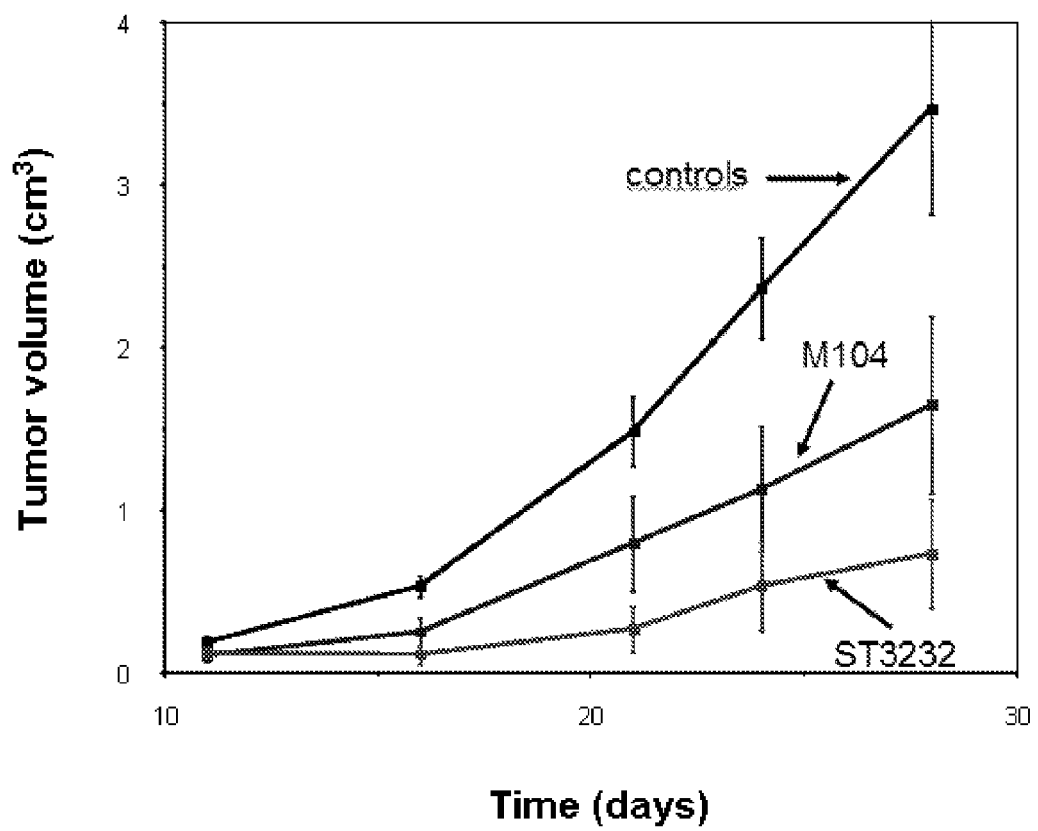

FIG. 9: Xenogenic transplant in nude mice and treatment with ST3232/10 in comparison with M104 antibody. The human colon carcinoma cell line KM12-SM, natively expressing Trop-1, was subcutaneously transplanted in nude mice. Four treatments, once a week, with 200 µg of ST3232/10 (ST3232 group), M104 (M104 group) or the vehicle (control group) were performed starting from the day of the inoculum. Tumor progression was monitored until day 30.

METHODS

Hybridoma Cells

In order to generate a new hybridoma cell clone against EpCAM, Balb/c mice were immunized with the L murine fibrosarcoma cell line (Alberti S et al., 1988) stably transfected with the human EpCAM molecule (NCBI RefSeq NM_002354). Splenocytes from immunized mice were fused to Sp2/0Ag14 myeloma cells, by standard method (Cianfriglia M. et al., 1986) and the hybridoma population screened by cytofluorimetry on tumor cell lines expressing EpCAM such as HT29. EpCAM specific hybridomas were cloned by limiting dilution two times in FCS containing medium and four times in protein free medium (Animal Derived Component Free Medium HyClone, HyQRPerbio). One of the positive clones derived from the fourth limiting dilution cloning was named cST3232 and fermented in mini bioreactor. The stability of the cST3232 cell line was 98.65%. Therefore a positive clone, cST3232/10, was selected and amplified for further development.

Antibody

ST3232/10 is a mouse immunoglobulin of IgG1/k isotype as determined by a commercial kit (Roche, Germany). Kappa light chain variable region was amplified from circularized cDNA using a couple of primers (5'-TGTCAAGAGCT-TCAACAGGA-3' (SEQ ID NO:13), 5'-AAGATGGATA-CAGTTGGTGC-3' (SEQ ID NO:14)) that anneal to antibody constant region as described in M. Sassano et al (1994).

Gamma heavy chain variable region was amplified from circularized cDNA using the primers oligonucleotide mouse γ1CH1 5'-ATGGAGTTAGTTTGGGCAGCAG-3'(SEQ ID NO:15) and oligonucleotide mouse γ1CH3 5'-GCACAAC-CACCATACTGAGAAG-3' (SEQ ID NO:16) that anneal to antibody constant region as described in M. Sassano et al. (1994).

PCR was performed using the following conditions: 40 sec at 94° C., 40 sec at 62° C., 1 min at 72° C. for 30 cycles.

The amplified fragments were cloned directly in PCRII cloning vector using TA cloning kit dual promoter PCRII (Invitrogen, #K2050-01). Nine clones containing kappa light chain and 7 clones containing gamma heavy chain variable regions were sequenced. Sequencing was carried out at MWG Biotech, Germany. Both strands were sequenced. No ambiguities were found.

SDS-PAGE Analysis

The antibody was run on a 4-12% gradient Bis Tris NuPAGE with 1×MES as running buffer and stained with Comassie solution (all reagents from Invitrogen, USA), under not reducing conditions and reducing conditions.

Chromatographic Profile

ST3232/10 was run on a TSGK3000 column (Tosoh Bioscience GmbH, Stuttgart, Germany) at the flow rate of 1 ml/min with PBS+NaN3 0.05% as running buffer.

Cell Transfection

Transfection with Trop-1 or Trop 2 was performed according to Alberti S et al., 1988.

FACS Analysis

The ST3232/10 antibody binding to native Trop-1 molecules on the surface of cells was analysed by flow cytometry on a panel of human cell lines. The reaction was carried out in 96-well plates with V bottom, in two steps using about $3*10^5$ cells per well. Cell suspensions were first incubated with 1 μg/well of ST3232/10 antibody; then, with 2 μl of a secondary PE-conjugated anti-mouse antibody (550589, BD Pharmingen, Erembodegem, Belgium). Cells were incubated for 30 min at 4° C. for each step, and washed with PBS containing 1% FCS. After final washing, cells were resuspended in PBS for acquisition and analysis using a FACSArray instrument with dedicated software (BD Biosciences, Erembodegem, Belgium). Other Trop1, Trop2 or irrelevant antibodies were used as controls and 7-AAD (BD Biosciences, Erembodegem, Belgium), was added to the samples (5 μl/$10^6$ cells) for vitality staining.

Confocal Microscopy

The breast tumor cell line MCF7 was stained by Alexafluor-488 labelled ST3232/10 and analysed by confocal microscopy. MCF7 cells were plated on 15×15 mm cover slips, and fixed after 48 h by incubation in PBS/4% paraformaldehyde for 30 min at room temperature. Following permeabilization for 30 min at room temperature in SM (10% serum in PBS) with 0.05% Saponin, the primary antibody (1 ug ST3232-Alexa488 per slide) was incubated 30 min at room temperature in SM+Saponin. After 3 washes in SM, cover slips were mounted for confocal microscopy observation.

Cell ELISA

A 96 well plate was initially blocked with 200 μl/well of 1×PBS, 10% FCS for 30 minutes at 37° C. and then seeded with 250.000 cells/well plus the primary antibody in a total volume of 100 μl. The plate was incubated for 1 hour at 37° C. and then washed three times with 1×PBS, 1% FCS by centrifugation at 2000 rpm for a few seconds. An anti mouse IgG Alkaline Phosphatase conjugated (Sigma A2429, 1/1000 dilution), was added to the primary antibody-cell complex and incubated for 1 hour at room temperature, then, after five washings, 200 μl of pNpp substrate (Sigma A3496) were added to each well and incubated for 30 minutes at 37°. The plate was finally centrifuged and 170 μl of supernatant transferred to a new plate and read at 405 nm with an ELISA spectrophotometer (SEAC Sirio S).

Surface Plasmonic Resonance

The affinity of ST3232/10 for EpCAM was evaluated by surface plasmonic resonance (SPR, Biacore X, Biacore, Uppsala, Sweden) immobilizing on a CM5 chip the commercially available chimeric fusion protein Fc-EpCAM extracellular domain (R&D, USA). The curves obtained injecting ST3232/10 in a concentration range of 500-7.8 nM were evaluated by means of the bivalent model (Biaevaluation software, v. 3.1, Biacore, Uppsala, Sweden).

Immunohistochemistry

Frozen sections from TRISTAR Technology laboratories (USA) with 35 sections of lung cancer and 10 normal lung (cod. #49561006), 35 colon-rectum cancer and 10 normal colon (cod. #49561004), 35 ovarian cancer and 10 normal (cod. #49561006) and slides with normal tissue (cod. #49561001) were utilized for selectivity study. ST3232/10 was diluted to 5 μg/mL in blocking solution (PBS+2.5% of normal horse serum). Isotype matching negative control was used on replica slides at the same concentration of test items.

Slides were processed according to manufacture's instruction and antibody binding revealed by the use of Vectastain ABC Elite Kit cod. PK6102 kit (Vector Laboratories). After hydration of tissue, quenching of endogenous peroxidase was performed by immersion of slides in 0.3% hydrogen peroxidase solution for 5 minutes. After washing in PBS for 5 minutes×3 times and blocking of the section with PBS+2.5% horse normal serum, primary antibody diluted in blocking solution at 5 μg/mL was added for 2 hrs at room temperature. After 3 washing with PBS slides were incubate with secondary goat anti mouse biotin conjugated antibody for 30 minutes and then with Avidin-Biotin Complex peroxidase—for 30 minutes. After additional washing slides were incubated in fresh DAB solution in Vector® DAB/Ni substrate kit (Cat. SK-4100) for 2 minutes and reaction was stopped in tap water. Counterstaining was made by immersion in Meyer's hematoxylin for 10 seconds. Finally slides were dehydrated in 75%, 80%, 95% and 100% ethanol for 1 min each, cleared in xylene and permanently mounted with synthetic mountant and observed with microscope.

In Vivo Model: Allotransplant in Nude Athymic Mice

The murine L fibrosarcoma cell line, transfected with Trop-1 (L/Trop-1) or not transfected (L/vector) with human Trop-1, was subcutaneously injected in three groups of nude athymic mice (10 animals/group). The day of the inoculum the animals were treated with 200 μg of ST3232/10 (L/vector+ST3232 and L/Trop-1+ST3232), Edrecolomab (L/Trop-1+Panorex) or unrelated murine IgG (L/vector and L/Trop-1). Other three administrations were performed at day 7, 15 and 22 as indicated by the arrows. In all groups the tumor growth was evaluated by caliper measurements up to day 50.

In Vivo Model: Xenotransplant of a Human Colorectal Cell Line

The human colon carcinoma cell line KM12-SM, natively expressing Trop-1, was subcutaneously transplanted in nude mice. Four treatments, once a week, with 200 μg of ST3232/10 (ST3232 group), M104 (M104 group) or the vehicle (control group) were performed starting from the day of the inoculum. Tumor progression was monitored until day 30.

Results

The sequence of ST3232/10 variable heavy chain (VH) complementary determining regions and of variable light chain (VL) complementary determining regions are shown in Table I.

TABLE I

Sequences of VH and VL complementary determining regions of ST3232/10 antibody.

| | Nucleotide sequences | Amino Acid sequences |
|---|---|---|
| Variable Heavy Chain | | |
| CDR1 | AGCGGTTATTACTGGAAC (SEQ ID 1) | S G Y Y W N (SEQ ID 2) |

TABLE I-continued

Sequences of VH and VL complementary determining regions of ST3232/10 antibody.

| | Nucleotide sequences | Amino Acid sequences |
|---|---|---|
| CDR2 | TATATAAGTTACGACGGTAGGAAT AAGTACAACCCATATCTCAAAAAT (SEQ ID 3) | Y I S Y D G R N K Y N P Y L K N (SEQ ID 4) |
| CDR3 | GCCCTCGGGGGGATTACGATGCT TTGGACTGC (SEQ ID 5) | A L G G D Y D A L D C (SEQ ID 6) |
| Variable Light Chain | | |
| CDR1 | AAGGTCACTATGAGCTGCAAGTCC AGTCAGAGTCTGTTAAACAGTAGA AGTCAAAAGAACTACTTGACC (SEQ ID 7) | K V I M S C K S S Q S L L N S R S Q K N Y L I (SEQ ID 8) |
| CDR2 | TGGGCATCCACTAGGGAATCT (SEQ ID 9) | W A S T R E S (SEQ ID 10) |
| CDR3 | CAGAATGATTATATTTATCCGCTC ACG (SEQ ID 11) | Q N D Y I Y P L T (SEQ ID 12) |

ST3232/10 proved to be homogeneous for light and heavy chains composition as shown by SDS-PAGE analysis and chromatographic profile (FIGS. 1 and 2). Indeed, the antibody run in triplicate on a 4-12% gradient Bis Tris NuPAGE with 1×MES as running buffer and stained with Comassie solution (all reagents from Invitrogen, USA), under not reducing conditions (lanes 1-3) did show a band of the expected molecular weight (150 KDa). Under reducing conditions (lanes 4-6) only the two bands corresponding to heavy (50 KDa) and light (25 KDa) chains were visible thus showing absence of other contaminating products. This findings were confirmed by the chromatographic profile where a single homogeneous peak eluted from the ST3232/10 run on a TSGK3000 column is observed (FIG. 2).

ST3232/10 specificity for EpCAM family members was evaluated by FACS analysis on a murine cell line not expressing the antigen, transfected with EpCAM (TROP-1) or the high homologue molecule TROP2. As shown FIG. 3, ST3232/10 is specific towards EpCAM since it reacted only with Trop-1 positive cells (panel A) and not with Trop-1 negative cells such as L cells (panel G) or L-Trop2 cells (panel D). A similar result was observed with other EpCAM specific antibodies (panels B, E, H: M104; C, I: HT29/26). T16 antibody was used as positive control in TROP2-L cells (panel F).

In addition, ST3232/10 has comparable binding activity to other EpCAM antibodies such as M104 (Klein C. E. et al., 1990). Their efficient recognition of the native antigen has been demonstrated by a cytofluorimetric study on a panel of cancer cell lines where different levels of EpCAM molecule were observed (Table II).

TABLE II

FACS results obtained on a panel of tumor cell lines of various origin using ST3232/10 or the M104 anti-TROP-1 antibody.

| Cell line (ATCC No.) | Type of tumor | ST3232/10 | M104 |
|---|---|---|---|
| HT 29 (HTB-38) | coloncarcinoma | ++++ | ++++ |
| LoVo (CCL-229) | " | ++++ | ++++ |
| COLO320DMF | " | nd | – |
| SW 620 (CCL-227) | " | ++++ | ++++ |
| CACO-2 (HTB-37) | " | ++++ | ++++ |
| LS 174T (CL-188) | " | ++++ | ++++ |
| KB 3-1 (kindly provided by Dr. Cianfriglia, ISS, Italy) | nasofaringeal ca. | ++++ | ++++ |
| SKBR-3 (HTB-30) | breast cancer | ++++ | nd |
| MDA-MB-231 (HTB-26) | " | +++ | nd |
| MDA-MB-468 (HTB-132) | " | + | nd |
| MCF10-2A (CRL-10781) | " | +++ | nd |
| MCF7 (HTB-22) | " | +++ | +++ |
| SKOV-3 (HTB-77) | ovarian ca. | + | nd |
| NIH:OVCAR3 (HTB-161) | " | ++++ | ++++ |
| IGROV-1 (Tumor National Inst., Italy) | " | – | – |
| SKMEL28 (HTB-72) | melanoma | – | nd |
| U-118 MG (HTB-15) | glioblastoma | – | nd |

++++ 100% positive,
+++ >90% positive,
++ >50% positive,
+ >20% positive,
+/– <15% positive,
– negative,
nd = not determined The breast tumor cell line MCF7 was stained by Alexafluor-488 labelled ST3232/10 and analysed by confocal microscopy (FIG. 4). The Alexa488-ST3232/10 conjugate demonstrates the expected pattern of staining, with highest intensity at cell-cell borders, and staining of isolated patches (two examples shown in FIGS. 4A and B).

The immunoreactivity of ST3232/10 was evaluated by cell-ELISA in comparison to other available anti-EpCAM antibodies on tumor cell lines naturally expressing EpCAM or transfected with the human transcript. As an example, the cell-ELISA on HT29 human colon carcinoma cell line of ST3232/10 and HT29/26 (Klein CE et al., 1990) anti-EpCAM antibodies is shown in FIG. 5. ST3232/10 is able to bind the naturally expressed EpCAM on HT29 cells in a dose dependent way. In this assay, HT29/26 appears to bind EpCAM with higher affinity than ST3232/10 as other antibodies do (data not shown).

The affinity of ST3232/10 for EpCAM was evaluated by surface plasmonic resonance (SPR). The curves obtained injecting ST3232/10 in a concentration range of 500-7.8 nM were evaluated by means of a bivalent model (FIG. 6A) and show a good quality fit as confirmed by chi$^2$ (1.97) and residuals <10% of the highest RU value (140) recorded in the experiment (FIG. 6B). $K_D$ of ST3232/10 resulted of 9.3E–10 ($k_{on}$=7.75E+04±297; $k_{off}$=7.2E–05±8.48E–06). The affinity of ST3232/10 for EpCAM is 274 times higher than the SPR-evaluated affinity displayed by Edrecolomab ($K_D$ 2.55E–07, Naundorf et al., 2002) while no affinity information are available for other anti-Trop-1 antibodies known in the literature.

Regarding the internalization of ST3232/10, a FACS test was performed by incubating the antibody with an EpCAM expressing cell line at 4° C. and then bringing the complex at 37° C. in a time range of 30-120 minutes. No differences were observed in the percentage of positive cells or in the mean fluorescence intensity of the 37° C.-incubated samples with respect to the control sample at 4° C. (Table III), thus indicating lack of internalization of the EpCAM/antibody complex.

TABLE III

Evaluation of ST3232/10 internalization in LoVo cell line.

|  | Positive % parent | MFI |
|---|---|---|
| 4° C. (control) | 98.5 | 3959 |
| 30' at 37° C. | 99.2 | 4182 |
| 60' at 37° C. | 98.1 | 4092 |
| 120' at 37° C. | 98.2 | 4149 |

The selectivity of ST3232/10 was investigated by immunohistochemistry on tissue micro-array sections representative of several solid tumors and normal tissues. The results are summarized in Tables IV and V and examples are shown in FIG. 7.

TABLE IV

ST3232/10 reactivity on tumours

|  | N° of cases | Positives (%) |
|---|---|---|
| Lung | 32 | 19 (59.3%) |
| Colon | 34 | 32 (94.1%) |
| Ovary | 35 | 31 (88.6%) |
| Total of examined tissues | 101 | 82 (81.2%) |

TABLE V

ST3232/10 reactivity on normal tissues

|  | N° of cases | Positives (%) |
|---|---|---|
| Lung | 8 | 1 (12.5%) |
| Colon | 8 | 5 (62.5%) |
| Ovary | 8 | 0 (0%) |
| Total of examined tissues | 24 | 6 (25.0%) |

Cryostatic tumor slides of high incidence solid cancer types (table IV) were evaluated in comparison to slides derived from histotype matched normal organs (table V). ST3232/10 is able to bind almost all colon (94.1%) and ovary (88.6%) carcinoma tested samples and the majority of lung (59.3%) carcinoma slides. The selectivity of ST3232/10 towards cancer cells was very high for ovarian specimens where none of the normal tissues reacted with the antibody while 88.6% of tumor samples were positive to ST3232. In addition, ST3232/10 reacted with higher incidence and stronger staining to cancer versus normal cells in the other tumor types. The selectivity for colon and lung tumors versus normal tissues is shown in FIG. 7, with clearly positive reaction on tumor tissues overexpressing EpCAM and negative staining of normal tissues.

Two different animal models were used for exploring the in vivo antibody activity on tumor cell growth. In the first experiment, three groups of nude athymic mice (10 animals/group) were subcutaneously (s.c.) transplanted with the murine fibrosarcoma L-hTrop-1 cell line and treated with ST3232/10, Edrecolomab or unrelated murine IgG once a week (200 µg/mouse) for 4 weeks, starting from the day of the inoculum. L cells not transfected with EpCAM were transplanted in two additional groups and the animals treated with ST3232/10 or control antibody. As shown in FIG. 8, EpCAM expressing tumor (L/Trop) had a more rapid development when compared to the un-transfected tumors (L/Vector or L/Vector+ST3232). In addition, ST3232/10 completely and permanently inhibited the growth of the EpCAM expressing tumor and did not interfer with the growth of the EpCAM negative tumor. On the other hand, edrecolomab (Panorex) also altered the growth of the EpCAM expressing tumor. However the tumor rapidly grew upon discontinuation of edrecolomab treatment.

A second animal model of nude mice xenotransplanted with a human colorectal cell line, KM12SM, was used to extend and confirm the previous results. The mice were treated with ST3232/10, murine IgG and another anti-EpCAM antibody, M104, with doses and schedule identical to that of the previous experiment (Table VI, FIG. 9). As indicated Table VI, tumor rate in the ST3232/10 treated group was lower (56%) than in the other two groups (90-100%).

TABLE VI

Tumor take rate

|  | Tumor take rate (%) |
|---|---|
| Controls | 100 |
| M104 | 90 |
| ST3232/10 | 56 |

In addition, as shown FIG. 9, ST3232/10 reduced tumor growth and increased the latency for developing tumor compared to the other groups. Theses results support the hypothesis of a direct therapeutic effect of ST3232/10 other than a simple binding to the target molecule.

REFERENCES

Alberti S et al., 1988, PNAS 85: 8391-8394

Burak W E Jr et al., 2001, Tumori 87: 142-146

Cianfriglia M. et al., 1986, Methods Enzymol. 121: 193210

De Bono J S et al., 2004, Clin Cancer Res 10: 7555-7565

Di Massimo A. M. et al., 1997, Br J Cancer 75: 822-828

Ferrer C. et al., 1996, J. Biotechnol. 52: 51-60

Frodin J E et al., 2002, Hybrid Hybridomics 21: 99-101

Goshorn S et al., 2001, Cancer Biot Radiopharm 16: 109-123

Klein C E et al., 1990, J Invest Dermatol 95: 74-82.

Naundorf S et al., 2002, Int J Cancer 100: 101-110

Oberneder R et al., 2006, Eur J Cancer 42: 2530-8

Old, L J, 1996, Sci Am 275: 136-143.

Paganelli et al., 1999, Eur J Nucl Med 26: 348-357

Parente D. et al., 1997, Anticancer Research 17: 4073-4074

Paul, W. E., Fundamental Immunology, Raven Press, NY, N.Y. 1993, chapter 23

Penichet M L. et al., 1999, J. Immunol., 163: 4421-4426

Prang N et al., 2005, Br J Cancer 92: 342-9

Punt C J et al., 2002, Lancet 360: 671-7

Riethmuller G et al., 1998, J Clin Oncol 16: 1788-1794

Sassano et al., 1994, Nucleic Acids Res 22: 1768-1769

Spizzo G et al., 2004, Breast Cancer Res Treat 86: 207-213

Velders et al., 1998, Br J Cancer 78: 478-483

Weiner L M et al., 1993, J Immunother 13: 110-116

Went et al., 2006, Br J Cancer, 94: 128-35

Winter M J et al., 2003, AJP 163: 2139-2148

The invention claimed is:

1. An isolated or purified anti-EpCAM antibody or a functional derivative thereof, wherein:
   the variable region of the antibody heavy chain comprises complementarity determining regions (CDRs) having sequences: SEQ ID No.2; SEQ ID No.4; and SEQ ID No.6, and
   the variable region of the antibody light chain comprises complementarity determining regions (CDRs) having sequences: SEQ ID No.8; SEQ ID No. 10; and SEQ ID No. 12.

2. The anti-EpCAM antibody or functional derivative thereof according to claim 1, wherein the anti-EpCAM antibody or functional derivative thereof is able to completely and permanently inhibit growth of EpCam expressing tumors.

3. The anti-EpCAM antibody according to claim 1, wherein the anti-EpCAM antibody or functional derivative thereof is a monoclonal antibody.

4. The anti-EpCAM antibody according to claim 3, wherein the anti-EpCAM antibody or functional derivative thereof is produced by the hybridoma cell line deposited according to the Budapest Treaty at the Advanced Biotechnology Center, Genoa, Italy, under No. PD06004.

5. The anti-EpCAM antibody according to claim 1, wherein the antibody is a scFv, an Fv fragment, a Fab fragment, a F(ab)2 fragment, a multimeric antibody, a peptide or a proteolytic fragment containing the epitope binding region.

6. The anti-EpCAM antibody according to claim 1, wherein the antibody is a chimeric protein, a fusion protein, or linked to an agent or a marker.

7. The anti-EpCAM antibody according to claim 6, wherein the chimeric protein is a mouse-human chimera.

8. The anti-EpCAM antibody according to claim 6, wherein the fusion protein comprises a cytokine, a protein of the avidin family, biotin, labelled biotin or other effector proteins.

9. The anti-EpCAM antibody according to claim 1, wherein the antibody is a humanised antibody.

10. An hybridoma cell line producing the anti-EpCAM antibody according to claim 1.

11. The hybridoma cell line according to claim 10, wherein the hybridoma cell line is the hybridoma deposited according to the Budapest Treaty at the Advanced Biotechnology Center, Genoa, Italy, under No. PD06004.

12. A medicament comprising the anti-EpCAM antibody of claim 1.

13. The medicament of claim 12 wherein the medicament is an anti-tumour medicament.

14. The medicament of claim 13, wherein the tumour is selected from the group consisting of: colon carcinoma, breast carcinoma, gastric carcinoma, ovary carcinoma, urinary bladder carcinoma and lung carcinoma.

15. A pharmaceutical composition comprising an effective amount of the antibody or derivatives thereof according to claim 1 and a pharmaceutically acceptable carrier or diluent.

16. The pharmaceutical composition of claim 15, wherein the pharmaceutical composition is suitable to be used in radioimmunotherapy.

17. The pharmaceutical composition according to claim 15, the composition further comprising in the same unit dose or separately, at least another tumour specific antibody.

18. The pharmaceutical composition according to claim 17, wherein the tumour specific antibody is an EpCAM antibody different from the antibody of claim 1.

19. A diagnostic product comprising the anti-EpCAM antibody of claim 1.

20. The diagnostic product of claim 19, wherein the diagnostic product is suitable for use as an anti-tumour diagnostic.

21. The diagnostic product of claim 20, wherein the diagnostic product is suitable for use as an anti-tumour diagnostic in vivo.

22. An injectable soluble composition for in vivo tumour diagnostics comprising the diagnostic product according to claim 21.

23. A diagnostic kit comprising
   an antibody or derivative thereof according to claim 1 and antigen-antibody complex detecting means
   for simultaneous, sequential or separate use in immunodetection of an antigen in a sample.

24. An isolated or purified nucleic acid, wherein the nucleic acid
   encodes the antibody or functional derivatives thereof according to claim 1, or
   consists of a degenerated sequence thereof.

25. The nucleic acid according to claim 24, comprising SEQ ID No.1, SEQ ID No.3, SEQ ID No.5, SEQ ID No.7, SEQ ID No.9 and SEQ ID No. 11.

26. An expression vector comprising the nucleic acid according to claim 24.

27. A host cell transformed with the expression vector according to claim 26.

28. A method for immunodetecting an antigen in a sample, the antigen able to bind to the antibody or derivative thereof according to claim 1, the method comprising the step of
   incubating in proper condition the sample with the antibody or derivative thereof to have an antigen-antibody complex, and
   detecting the antigen-antibody complex.

29. A method for treating a tumor expressing EpCAM in a subject, the method comprising administering to the subject the anti-EpCAM antibody of claim 1.

30. A method for diagnosing a tumor expressing Ep-CAM in a subject, the method comprising administering to the subject the anti-EpCAM antibody of claim 1 and detecting formation of an antigen-anti-EpCAM antibody in the subject.

* * * * *

SEQUENCE LISTING

<160> NUMBER OF SEQ ID NOS: 16

<210> SEQ ID NO 1
<211> LENGTH: 18
<212> TYPE: DNA
<213> ORGANISM: Artificial
<220> FEATURE:
<223> OTHER INFORMATION: synthetic CDR1 VH
<220> FEATURE:
<221> NAME/KEY: CDS
<222> LOCATION: (1)..(18)

<400> SEQUENCE: 1 agc ggt tat tac tgg aac                                             18
Ser Gly Tyr Tyr Trp Asn
1               5

<210> SEQ ID NO 2
<211> LENGTH: 6
<212> TYPE: PRT
<213> ORGANISM: Artificial
<220> FEATURE:
<223> OTHER INFORMATION: Synthetic Construct

<400> SEQUENCE: 2

Ser Gly Tyr Tyr Trp Asn
1               5

<210> SEQ ID NO 3
<211> LENGTH: 48
<212> TYPE: DNA
<213> ORGANISM: Artificial
<220> FEATURE:
<223> OTHER INFORMATION: synthetic CDR2 VH
<220> FEATURE:
<221> NAME/KEY: CDS
<222> LOCATION: (1)..(48)

<400> SEQUENCE: 3 tat ata agt tac gac ggt agg aat aag tac aac cca tat ctc aaa aat    48
Tyr Ile Ser Tyr Asp Gly Arg Asn Lys Tyr Asn Pro Tyr Leu Lys Asn
1               5                   10                  15

<210> SEQ ID NO 4
<211> LENGTH: 16
<212> TYPE: PRT
<213> ORGANISM: Artificial
<220> FEATURE:
<223> OTHER INFORMATION: Synthetic Construct

<400> SEQUENCE: 4

Tyr Ile Ser Tyr Asp Gly Arg Asn Lys Tyr Asn Pro Tyr Leu Lys Asn
1               5                   10                  15

<210> SEQ ID NO 5
<211> LENGTH: 33
<212> TYPE: DNA
<213> ORGANISM: Artificial
<220> FEATURE:
<223> OTHER INFORMATION: synthetic CDR3 VH
<220> FEATURE:
<221> NAME/KEY: CDS
<222> LOCATION: (1)..(33)

<400> SEQUENCE: 5 gcc ctc ggg ggg gat tac gat gct ttg gac tgc                        33
Ala Leu Gly Gly Asp Tyr Asp Ala Leu Asp Cys
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic Construct

<400> SEQUENCE: 6

Ala Leu Gly Gly Asp Tyr Asp Ala Leu Asp Cys
1               5                   10

<210> SEQ ID NO 7
<211> LENGTH: 69
<212> TYPE: DNA
<213> ORGANISM: Artificial
<220> FEATURE:
<223> OTHER INFORMATION: synthetic CDR1 VL
<220> FEATURE:
<221> NAME/KEY: CDS
<222> LOCATION: (1)..(69)

<400> SEQUENCE: 7 aag gtc act atg agc tgc aag tcc agt cag agt ctg tta aac agt aga     48
Lys Val Thr Met Ser Cys Lys Ser Ser Gln Ser Leu Leu Asn Ser Arg
1               5                   10                  15 agt caa aag aac tac ttg acc                                         69
Ser Gln Lys Asn Tyr Leu Thr
            20

<210> SEQ ID NO 8
<211> LENGTH: 23
<212> TYPE: PRT
<213> ORGANISM: Artificial
<220> FEATURE:
<223> OTHER INFORMATION: Synthetic Construct

<400> SEQUENCE: 8

Lys Val Thr Met Ser Cys Lys Ser Ser Gln Ser Leu Leu Asn Ser Arg
1               5                   10                  15

Ser Gln Lys Asn Tyr Leu Thr
            20

<210> SEQ ID NO 9
<211> LENGTH: 21
<212> TYPE: DNA
<213> ORGANISM: Artificial
<220> FEATURE:
<223> OTHER INFORMATION: synthetic CDR2 VL
<220> FEATURE:
<221> NAME/KEY: CDS
<222> LOCATION: (1)..(21)

<400> SEQUENCE: 9 tgg gca tcc act agg gaa tct                                         21
Trp Ala Ser Thr Arg Glu Ser
1               5

<210> SEQ ID NO 10
<211> LENGTH: 7
<212> TYPE: PRT
<213> ORGANISM: Artificial
<220> FEATURE:
<223> OTHER INFORMATION: Synthetic Construct

<400> SEQUENCE: 10

Trp Ala Ser Thr Arg Glu Ser
1               5

<210> SEQ ID NO 11
<211> LENGTH: 27
<212> TYPE: DNA
<213> ORGANISM: Artificial
<220> FEATURE:
<223> OTHER INFORMATION: synthetic CDR3 VL
<220> FEATURE:
<221> NAME/KEY: CDS
<222> LOCATION: (1)..(27)

<400> SEQUENCE: 11 cag aat gat tat att tat ccg ctc acg                          27
Gln Asn Asp Tyr Ile Tyr Pro Leu Thr
1               5

<210> SEQ ID NO 12
<211> LENGTH: 9
<212> TYPE: PRT
<213> ORGANISM: Artificial
<220> FEATURE:
<223> OTHER INFORMATION: Synthetic Construct

<400> SEQUENCE: 12

Gln Asn Asp Tyr Ile Tyr Pro Leu Thr
1               5

<210> SEQ ID NO 13
<211> LENGTH: 20
<212> TYPE: DNA
<213> ORGANISM: Artificial
<220> FEATURE:
<223> OTHER INFORMATION: synthetic primer

<400> SEQUENCE: 13
tgtcaagagc ttcaacagga                                        20

<210> SEQ ID NO 14
<211> LENGTH: 20
<212> TYPE: DNA
<213> ORGANISM: Artificial
<220> FEATURE:
<223> OTHER INFORMATION: synthetic primer

<400> SEQUENCE: 14
aagatggata cagttggtgc                                        20

<210> SEQ ID NO 15
<211> LENGTH: 22
<212> TYPE: DNA
<213> ORGANISM: Artificial
<220> FEATURE:
<223> OTHER INFORMATION: synthetic primer

<400> SEQUENCE: 15
atggagttag tttgggcagc ag                                     22

<210> SEQ ID NO 16
<211> LENGTH: 22
<212> TYPE: DNA
<213> ORGANISM: Artificial
<220> FEATURE:
<223> OTHER INFORMATION: synthetic primer

<400> SEQUENCE: 16
gcacaaccac catactgaga ag                                     22